United States Patent [19]

Lin

[11] 4,042,607

[45] Aug. 16, 1977

[54] 4,4,5,5-TETRADEHYDRO-PGF$_{1\alpha}$ ANALOGS

[75] Inventor: Chiu-Hong Lin, Portage, Mich.

[73] Assignee: The Upjohn Company, Kalamazoo, Mich.

[21] Appl. No.: 738,719

[22] Filed: Nov. 4, 1976

Related U.S. Application Data

[62] Division of Ser. No. 619,077, Oct. 2, 1975, Pat. No. 4,013,695.

[51] Int. Cl.$^2$ ............................................. C07C 177/00
[52] U.S. Cl. ............................ 260/410.9 R; 260/408; 260/413; 260/468 D; 260/514 D
[58] Field of Search ............. 260/468 D, 514 D, 408, 260/410.9 R, 413

[56] References Cited

U.S. PATENT DOCUMENTS 3,933,889  1/1976  Magerlin .............................. 260/468

Primary Examiner—Robert Gerstl
Attorney, Agent, or Firm—Robert A. Armitage

[57] ABSTRACT

This invention comprises certain analogs of the prostaglandins in which there is a triple bond between C-5 and C-6 or C-4 and C-5. Also provided in this invention, are novel chemical processes useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

32 Claims, No Drawings

4,4,5,5-TETRADEHYDRO-PGF$_{1\alpha}$ ANALOGS

The present application is a divisional application of Ser. No. 619,077, filed Oct. 2, 1975, now issued as U.S. Pat. No. 4,013,695, on Mar. 22, 1977.

The present invention relates to prostaglandin analogs for which the essential material constituting a disclosure therefor is incorporated by reference here from U.S. Pat. No. 4,013,695, issued Mar. 22, 1977.

I claim:

1. A prostaglandin analog of the formula

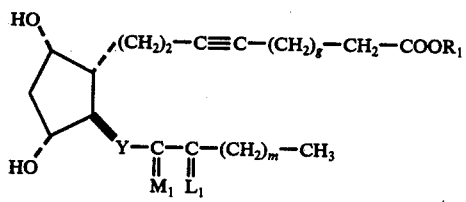

wherein g is one, 2, or 3;
wherein Y is trans—CH=CH—;
wherein M$_1$ is

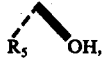

or

wherein R$_5$ is hydrogen or methyl;
wherein m is one to 5, inclusive;
wherein L$_1$ is

or a mixture of

and wherein R$_3$ and R$_4$ are hydrogen, methyl, or fluoro, being the same or different, with the proviso that one of R$_3$ and R$_4$ is fluoro only when the other is hydrogen or fluoro; and
wherein R$_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation.

2. A compound according to claim 1, wherein M$_1$ is

3. A compound according to claim 1, wherein M$_1$ is

4. A compound according to claim 3, wherein g is 3.
5. A compound according to claim 4, wherein m is 3.
6. A compound according to claim 5, wherein R$_3$, R$_4$, and R$_5$ are all hydrogen.
7. 2a,2b-Dihomo-4,4,5,5-tetradehydro-PGF$_{1\alpha}$, methyl ester, a compound according to claim 6.
8. A compound according to claim 3, wherein g is one.
9. A compound according to claim 8, wherein m is 3.
10. A compound according to claim 9, wherein R$_3$ and R$_4$ are both hydrogen.
11. A compound according to claim 10, wherein R$_5$ is methyl.
12. 4,4,5,5-Tetradehydro-15-methyl-PGF$_{1\alpha}$, methyl ester, a compound according to claim 11.
13. 4,4,5,5-Tetradehydro-15-methyl-PGF$_{1\alpha}$, a compound according to claim 11.
14. A compound according to claim 10, wherein R$_5$ is hydrogen.
15. 4,4,5,5-Tetradehydro-PGF$_{1\alpha}$, a compound according to claim 14.
16. 4,4,5,5-Tetradehydro-PGF$_{1\alpha}$, methyl ester, a compound according to claim 14.
17. A compound according to claim 9, wherein at least one of R$_3$ and R$_4$ is methyl.
18. A compound according to claim 17, wherein R$_3$ and R$_4$ are both methyl.
19. A compound according to claim 18, wherein R$_5$ is methyl.
20. 4,4,5,5-Tetradehydro-15,16,16-trimethyl-PGF$_{1\alpha}$, a compound according to claim 19.
21. 4,4,5,5-Tetradehydro-15,16,16-trimethyl-PGF$_{1\alpha}$, methyl ester, a compound according to claim 19.
22. A compound according to claim 18, wherein R$_5$ is hydrogen.
23. 4,4,5,5-Tetradehydro-16,16-dimethyl-PGF$_{1\alpha}$, a compound according to claim 22.
24. 4,4,5,5-Tetradehydro-16,16-dimethyl-PGF$_{1\alpha}$, methyl ester, a compound according to claim 22.
25. A compound according to claim 9, wherein at least one of R$_3$ and R$_4$ is fluoro.
26. A compound according to claim 25, wherein R$_3$ and R$_4$ are both fluoro.
27. A compound according to claim 26, wherein R$_5$ is methyl.
28. 4,4,5,5-Tetradehydro-15-methyl-16,16-difluoro-PGF$_{1\alpha}$, a compound according to claim 27.
29. 4,4,5,5-Tetradehydro-15-methyl-16,16-difluoro-PGF$_{1\alpha}$, methyl ester, a compound according to claim 27.
30. A compound according to claim 26, wherein R$_5$ is hydrogen.
31. 4,4,5,5-Tetradehydro-16,16-difluoro-PGF$_{1\alpha}$, a compound according to claim 30.
32. 4,4,5,5-Tetradehydro-16,16-difluoro-PGF$_{1\alpha}$, methyl ester, a compound according to claim 30.

* * * * *